(12) United States Patent
Li et al.

(10) Patent No.: US 10,537,417 B2
(45) Date of Patent: Jan. 21, 2020

(54) DENSITY GRADIENT BIOPOLYMERIC MATRIX IMPLANTS

(71) Applicant: Collagen Matrix, Inc., Oakland, NJ (US)

(72) Inventors: Shu-Tung Li, Oakland, NJ (US); Natsuyo Shishido Lee, Oakland, NJ (US); Debbie Yuen, Woodcliff Lake, NJ (US)

(73) Assignee: Collagen Matrix, Inc., Oakland, NJ (US)

(*) Notice: Subject to any disclaimer, the term of this patent is extended or adjusted under 35 U.S.C. 154(b) by 338 days.

(21) Appl. No.: 15/204,517

(22) Filed: Jul. 7, 2016

(65) Prior Publication Data

US 2018/0008391 A1 Jan. 11, 2018

(51) Int. Cl.
*A61F 2/00* (2006.01)
*A61F 2/02* (2006.01)
*A61L 27/24* (2006.01)
*A61L 27/26* (2006.01)
*A61L 27/48* (2006.01)

(52) U.S. Cl.
CPC .............. *A61F 2/0077* (2013.01); *A61F 2/02* (2013.01); *A61L 27/24* (2013.01); *A61L 27/26* (2013.01); *A61L 27/48* (2013.01); *A61F 2002/009* (2013.01); *A61L 2430/34* (2013.01)

(58) Field of Classification Search
None
See application file for complete search history.

(56) References Cited

U.S. PATENT DOCUMENTS

| | | |
|---|---|---|
| 5,206,028 A | 4/1993 | Li |
| 5,306,311 A | 4/1994 | Stone et al. |
| 6,974,862 B2 | 12/2005 | Ringeisen et al. |
| 7,374,777 B2 | 5/2008 | Li et al. |

(Continued)

OTHER PUBLICATIONS

Vollmert, B., "The Form of the Macromolecule (Molecular Shape)", Polymer Chemistry, 1973, p. 451. (Year: 1973).*

(Continued)

*Primary Examiner* — Carlos A Azpuru
*Assistant Examiner* — Casey S Hagopian
(74) *Attorney, Agent, or Firm* — Cesari and McKenna, LLP (57) ABSTRACT

A density gradient biopolymeric matrix implant is disclosed. The implant includes a first homogeneous matrix layer and a second homogeneous matrix layer having a density different from that of the first homogeneous matrix layer. Biopolymeric fibers at the surface of the first homogeneous matrix layer are physically in contact with and cross-linked to the biopolymeric fibers at the surface of the second homogeneous matrix layer. Also disclosed is a three-dimensional density gradient biopolymeric matrix implant that includes a first homogeneous matrix surrounding a second homogeneous matrix having a different density. Biopolymeric fibers at an inner surface of the first homogeneous matrix are physically in contact with and cross-linked to biopolymeric fibers at an outer surface of the second homogeneous matrix. Furthermore, methods for preparing the density gradient biopolymeric matrix implant and the three-dimensional density gradient biopolymeric matrix implant are provided.

6 Claims, 2 Drawing Sheets

(56) References Cited

U.S. PATENT DOCUMENTS

| | | | |
|---|---|---|---|
| 7,807,192 | B2 | 10/2010 | Li et al. |
| 9,056,078 | B2 | 6/2015 | Bosley, Jr. et al. |
| 9,226,828 | B2 | 1/2016 | Bonutti |
| 2009/0269385 | A1 | 10/2009 | Zubery et al. |
| 2011/0270394 | A1 | 11/2011 | Herford et al. |
| 2013/0345826 | A1* | 12/2013 | Li .............................. A61F 2/28 623/23.58 |
| 2014/0025166 | A1* | 1/2014 | Bonutti .............. A61B 17/0218 623/13.12 |
| 2014/0112973 | A1* | 4/2014 | Steinberg ................ A61L 27/34 424/445 |

OTHER PUBLICATIONS

"Bulk Density and Porosity" accessed online on Jun. 22, 2019 at www.wmearthcare.com/everyday-soil-science-4-bulk-density-porosity. (Year: 2019).*

Lee et al "Two Novel Collagen Based Dura Repair Membranes: Solutions for the Multifaceted Needs in Duraplasty Part II: In Vivo Rabbit Duraplasty Studies" 10$^{th}$ World Biomaterial Congress, Montreal, Canada, May 2016. Abstract #3375.

Vollmert "The Form of the Macromolecule (Molecular Shape)" Polymer Chemistry, p. 451, 1973.

* cited by examiner

DENSITY GRADIENT BIOPOLYMERIC MATRIX IMPLANTS

BACKGROUND

Biopolymeric matrix implants have become important modalities for surgical and drug delivery applications, including but not limited to dura mater repair, burn therapy, wound care, guided tissue regeneration in orthopedic and dental surgeries, and controlled sustained drug delivery.

In a wound care application, a biopolymeric implant, e.g., a collagen membrane, can provide an active wound healing environment by supporting new tissue formation. Yet, an additional dressing is typically required to prevent or reduce bacterial invasion into the wound site. In the area of regenerative medicine and dentistry, biopolymeric matrix implants can be designed to provide appropriate mechanical properties, pore structures, and surface properties for either stimulating tissue ingrowth or preventing unwanted tissue growing into the implant in order to facilitate guided tissue regeneration.

The need exists for an implant having distinct density regions and capable of performing multiple roles after implantation. Such an implant should have the following properties: (i) a region of the implant is water or fluid-tight to prevent leakage of body fluid across the implant, (ii) the implant possesses regions of differential biomechanical properties, including tensile, tear, and peel strengths, (iii) the implant has a desirable degree of conformability, (iv) the implant facilitates cell ingrowth, is cell occlusive, or both, i.e., certain regions of the implant are cell occlusive and other areas are cell conductive, (v) the implant has certain in vivo resorption characteristics, namely, it has regions of differential resorption rates, and (vi) the implant can incorporate, in a particular region, bioactive molecules which can be controllably released in a sustained fashion.

SUMMARY

To address the needs mentioned above, a density gradient biopolymeric matrix implant is provided. The implant includes (i) a first homogeneous matrix layer having a particular density and formed of biopolymeric fibers, and (ii) a second homogeneous matrix layer having a density different from that of the first homogeneous matrix layer and also formed of biopolymeric fibers. The biopolymeric fibers at the surface of the first homogeneous matrix layer are physically in contact with and cross-linked to the biopolymeric fibers at the surface of the second homogeneous matrix layer.

Also provided is a three-dimensional density gradient biopolymeric matrix implant. The three-dimensional implant includes two matrices, a first homogeneous matrix and a second homogeneous matrix, which have different densities. Both of the matrices are formed of cross-linked biopolymeric fibers. In the three-dimensional density gradient biopolymeric matrix implant, the first homogeneous matrix encloses the second homogeneous matrix and the biopolymeric fibers at the inner surface of the first homogeneous matrix are physically in contact with and cross-linked to the biopolymeric fibers at the outer surface of the second homogeneous matrix.

Further disclosed is a method for preparing a density gradient biopolymeric matrix implant. The method includes the steps of (i) obtaining a first homogeneous biopolymeric matrix layer having a first density and having a first surface and a second surface opposed to the first surface, (ii) obtaining a second homogeneous biopolymeric matrix layer having a second density lower than the first density and having a first surface and a second surface opposed to the first surface, (iii) hydrating the first homogeneous biopolymeric matrix layer, (iv) placing in contact the first surface of the hydrated first homogeneous biopolymeric matrix layer with the first surface of the second homogeneous biopolymeric matrix layer to form a two-layer matrix, (v) freeze-drying the two-layer matrix, and (vi) cross-linking the freeze-dried two-layer matrix.

An alternative method includes the steps of (i) obtaining a first homogeneous biopolymeric matrix layer having a first density, (ii) preparing a dispersion of biopolymeric fibers, (iii) placing the first homogeneous biopolymeric matrix layer in contact with the dispersion to form a composite matrix, (iv) freeze-drying the composite matrix, and (v) cross-linking the freeze-dried composite matrix.

The details of one or more embodiments of the invention are set forth in the drawings and description below. Other features, objects, and advantages of the invention will be apparent from the description, the drawings, and from the claims. All references cited herein are hereby incorporated by reference in their entirety.

BRIEF DESCRIPTION OF THE DRAWINGS

The invention description below refers to the accompanying drawings, of which.

DETAILED DESCRIPTION

As mentioned above, a density gradient biopolymeric matrix implant is disclosed. The implant includes two or more homogeneous matrix layers having different densities. Each of the homogeneous matrix layers is formed of biopolymeric fibers, which are biocompatible and bioresorbable. The biopolymeric fibers can be prepared from many distinct biopolymeric molecules, preferably from proteins and polysaccharides.

In particular embodiments of the density gradient biopolymeric matrix implant, the biopolymeric fibers in one layer are different from the biopolymeric fibers in another layer. For example, one homogeneous matrix layer can be formed of biopolymeric fibers prepared from a protein and another homogeneous matrix layer can be formed of biopolymeric fibers prepared from a polysaccharide. In another embodiment, the biopolymeric fibers in all of the layers are of the same type. All of the biopolymeric fibers can be prepared from protein, or all of the biopolymeric fibers can be prepared from polysaccharides.

Examples of polysaccharides that can be used to form the biopolymeric fibers include alginic acid, chitosan, glycosaminoglycan, and cellulose. Exemplary proteins that can be used to produce the biopolymeric fibers include collagen, elastin, and fibrin.

Collagen is preferred for producing the biopolymeric fibers, in particular, fibrillar collagen (e.g., type I, type II, and type III collagen). The collagens can be genetically engineered collagens, collagen from human tissues, collagen from bovine or porcine tissues, and collagen from fish.

Type I collagen is particularly preferred, as it is biocompatible, available in large quantities, and easily purified by known methods. Type I collagen is readily extractable from animal tissues such as tendon, dermis, bone, and ligament. Methods for purifying collagen fibers have been well documented. See, e.g., U.S. Pat. No. 5,206,028 and Oneson, et al., J. Am. Leather Chemists Assoc. 65:440-450, 1970.

In a preferred embodiment of the density gradient biopolymeric matrix implant, all of the biopolymeric fibers are prepared from type I collagen.

As mentioned above, the density gradient biopolymeric matrix implant includes two or more homogeneous matrix layers. The phrase "homogeneous matrix layer" as used herein means that biopolymeric fibers in the layer are of a single type, are uniformly distributed within the layer, and the layer has a uniform thickness and density throughout. If a homogeneous matrix layer also includes bioactive molecules (see below), those bioactive molecules are evenly distributed throughout the layer.

The density gradient biopolymeric matrix implant described above includes two or more homogeneous matrix layers having different densities. For example, in a density gradient biopolymeric matrix implant having two homogeneous matrix layers, one region preferably has a density in the range of 0.3 g/cm$^3$ to 1.0 g/cm$^3$ and the other region can have a density in the range of 0.02 g/cm$^3$ to 0.3 g/cm$^3$. In another example, a density gradient biopolymeric matrix implant includes three homogeneous matrix layers, where one layer can have a density in the range of 0.6 g/cm$^3$ to 1.0 g/cm$^3$, a second layer can have a density in the range of 0.2 g/cm$^3$ to 0.6 g/cm$^3$, and a third layer can have a density in the range of 0.02 g/cm$^3$ to about 0.2 g/cm$^3$.

The density of a particular layer can be selected depending upon the intended use of the implant. A density gradient biopolymeric matrix implant containing two homogeneous matrix layers of distinctly different densities can be advantageously used for guided tissue regeneration and for facilitating wound healing. For example, a density gradient biopolymeric matrix implant can allow for cell infiltration into a specific region of the implant while impeding entry of cells into other regions of the implant, thus functioning as a scaffold for guided wound healing and functional tissue regeneration. In another example, a density gradient biopolymeric matrix implant can be used for the treatment of third degree burns. One homogeneous matrix layer of the implant is a low density porous matrix that can stimulate cell conduction and dermal tissue regeneration, and the second homogeneous matrix layer is a high density layer that protects against bacterial invasion and controls moisture in the wound. Since both matrices are bioresorbable and the rate of resorption can be controlled via chemical crosslinking (see below), the density gradient biopolymeric matrix implant can be designed as a temporary scaffold to guide dermal regeneration.

The density gradient biopolymeric matrix implant can also be designed for the repair of dura mater injuries in cranial and spinal surgeries. One homogeneous matrix layer is a porous matrix which is conformable, facilitates clotting, serves as a cushion to protect the brain, and supports the dura regeneration. The other homogeneous matrix layer is fluid-tight to prevent cerebral and spinal fluid leakage.

Each homogeneous matrix layer of the density gradient biopolymeric matrix implant can have a thickness of 1.0 μm to 50 mm. In an example of the density gradient biopolymeric matrix implant having two homogeneous matrix layers, one homogeneous matrix layer can have a thickness of 1.0 μm to 1.0 mm and the other homogeneous matrix layer can have a thickness of 0.1 mm to 50 mm.

The average pore size in each layer can be from less than 3 μm up to 500 μm. Again referring to the density gradient biopolymeric matrix implant having two homogeneous matrix layers, one homogeneous matrix layer can have a pore size less than 3 μm and the other homogeneous matrix layer can have a pore size of 50 μm to 500 μm.

In a particular aspect of a density gradient biopolymeric matrix implant having two homogeneous matrix layers, one homogeneous matrix layer has a thickness of 1.0 μm to 1.0 mm and a pore size less than 3 μm and the other homogeneous matrix layer has a thickness of 0.1 mm to 50 mm and a pore size of 50 μm to 500 μm.

Methods of engineering biopolymeric matrices having particular densities and pore sizes are well known in the field. See, e.g., U.S. Pat. Nos. 7,807,192; 7,374,777; and 5,306,311.

As set forth above, for a density gradient biopolymeric matrix implant having two homogeneous matrix layers, biopolymeric fibers on the surface of one homogeneous matrix layer are physically in contact with and cross-linked to the biopolymeric fibers on the surface of the other homogeneous matrix layer.

The biopolymeric fibers at the surface of the first homogeneous matrix layer are in close contact with biopolymeric fibers at the surface of the second homogeneous matrix layer such that fiber entanglement and physical trapping can occur. These physical and mechanical interactions are stabilized via covalent bonds, i.e., cross-links, between the surface biopolymeric fibers.

Functional groups present on the biopolymeric fibers can form cross-links either directly or via a chemical cross-linking agent. Amino, guanidino, hydroxyl, and carboxylic groups are the most common side chain groups of biopolymeric molecules. By selecting an appropriate chemical agent, intermolecular chemical bonds can be formed under controlled conditions.

If the biopolymeric fibers are formed of protein, they can be cross-linked via dehydrothermal cross-linking, in which an amino group of one biopolymer and a nearby carboxyl group from another biopolymer are condensed to form a peptide bond by removing a molecule of water.

Chemical cross-linking agents that can be used to cross-link biopolymeric fibers together are well known in the art. Crosslinking agents of low molecular weight and high vapor pressure such as formaldehyde, glyceraldehyde, glycolaldehyde, or glutaraldehyde can be used. In a preferred embodiment, cross-links are formed using formaldehyde.

Preferably, the chemical cross-linking does not significantly change the physical and chemical characteristics of the matrices in the density gradient biopolymeric implant. In this connection, to maintain close contact between the cross-linked fibers, higher molecular weight cross-linking agents are not used. For example, reducing sugars are excluded from among the cross-linking agents that can be used, i.e., the density gradient biopolymeric matrix implant is free of reducing sugars.

The density gradient biopolymeric matrix implant is both chemically and mechanically stable as a result of the cross-links between surface biopolymeric fibers on the homogeneous matrix layers. The chemical and mechanical stability is such that the homogeneous matrix layers cannot be separated by an external force without severely damaging them.

The stability of the density gradient biopolymeric matrix implant can be expressed as peel strength, i.e., the force necessary to separate two adjacent layers of the implant. The peel strength can be from 0.1 kgf/in to 2.0 kgf/in.

Figure 1A:
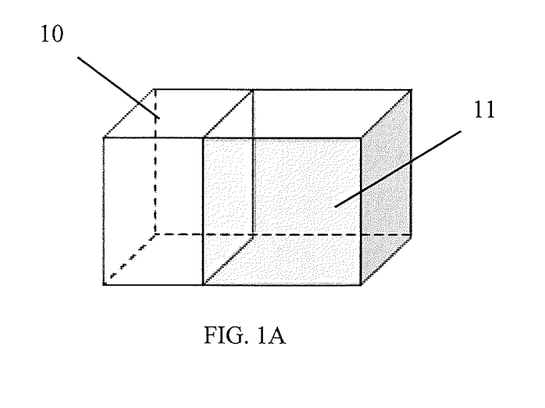
FIG. 1A is a three-dimensional view of one embodiment of a density gradient biopolymeric matrix implant having two different density regions arranged in a rectangular geometry.
Figure 1B:
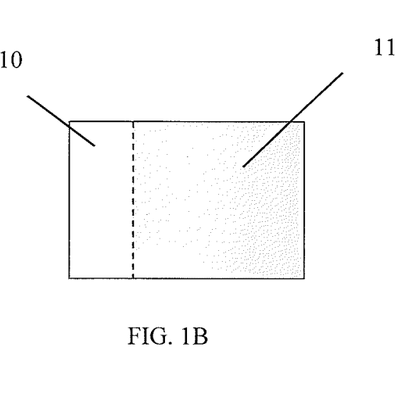
FIG. 1B is a cross-sectional view of the implant depicted in FIG. 1A.

FIGS. 1A and 1B depict an example of a density gradient biopolymeric matrix implant including two homogeneous matrix layers having different densities. Layer 10 can have a density in the range of 0.3 g/cm$^3$ to 1.0 g/cm$^3$, a thickness ranging from 1.0 μm to 1.0 mm, and a pore size less than 3 μm. Layer 11, on the other hand, can have a density in the range of 0.02 g/cm$^3$ to 0.3 g/cm$^3$, a thickness ranging from 0.1 mm to 50 mm, and a pore size of 50 μm to 500 μm.

The density gradient biopolymeric implants described above can have a shape advantageous for a particular application. For example, the density gradient biopolymeric implant can be rectangular in shape. This shape is useful for dura repair and for burn treatment.

A three-dimensional density gradient biopolymeric matrix implant is also provided. The three-dimensional density gradient biopolymeric matrix implant includes two or more homogeneous matrices having distinct densities. The homogeneous matrices are each formed of cross-linked biopolymeric fibers.

Biopolymeric fibers that can be used are the same as those set forth at page 5, lines 1-22, supra.

In a preferred embodiment of the three-dimensional density gradient biopolymeric matrix implant, all of the biopolymeric fibers are prepared from type I collagen.

In an embodiment of the three-dimensional density gradient biopolymeric matrix implant having two homogeneous matrices with differing densities, one homogeneous matrix encloses the other homogeneous matrix and biopolymeric fibers at the inner surface of the first homogeneous matrix are physically in contact with and cross-linked to the biopolymeric fibers at the outer surface of the second homogeneous matrix.

In a particular embodiment, the first homogeneous matrix completely encloses the second homogeneous matrix.

FIGS. 2A, 2B, 3A, and 3B depict two examples of a three-dimensional density gradient biopolymeric matrix implant including two homogeneous matrices having different densities. Matrices 20 and 30 can have a density in the range of 0.02 g/cm$^3$ to 0.3 g/cm$^3$, a thickness ranging from 0.1 mm to 50 mm, and a pore size of 50 μm to 500 μm. Matrices 21 and 31, on the other hand, can have a density in the range of 0.3 g/cm$^3$ to 1.0 g/cm$^3$, a thickness ranging from 1.0 μM to 1.0 mm, and a pore size less than 3 μm.

The three-dimensional density gradient biopolymeric matrix implant, as mentioned above, can have more than two homogeneous matrices, each of which has a distinct density. For example, in a three-dimensional density gradient biopolymeric matrix implant having three distinct homogeneous matrices, a first matrix can have a density in the range of 0.02 g/cm$^3$ to 0.2 g/cm$^3$, a second matrix can have a density in the range of 0.2 g/cm$^3$ to 0.6 g/cm$^3$, and a third matrix can have a density in the range of 0.6 g/cm$^3$ to 1.0 g/cm$^3$.

In an embodiment of the three-dimensional density gradient biopolymeric matrix implant having three homogeneous matrices with differing densities, a first homogeneous matrix encloses a second homogeneous matrix which in turn encloses a third homogeneous matrix. Biopolymeric fibers at the inner surface of the first homogeneous matrix are physically in contact with and cross-linked to the biopolymeric fibers at the outer surface of the second homogeneous matrix. Likewise, biopolymeric fibers at the inner surface of the second homogeneous matrix are physically in contact with and cross-linked to the biopolymeric fibers at the outer surface of the third homogeneous matrix.

In a particular embodiment, the first homogeneous matrix completely encloses the second homogeneous matrix and the second homogeneous matrix completely encloses the third homogeneous matrix.

Figure 4A:
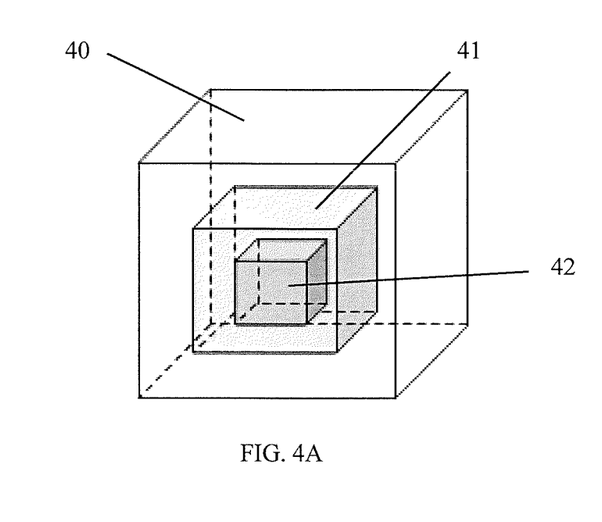
FIG. 4A is a three-dimensional view of an embodiment of a density gradient biopolymeric matrix implant having three different density regions arranged in a cubic geometry.
Figure 4B:
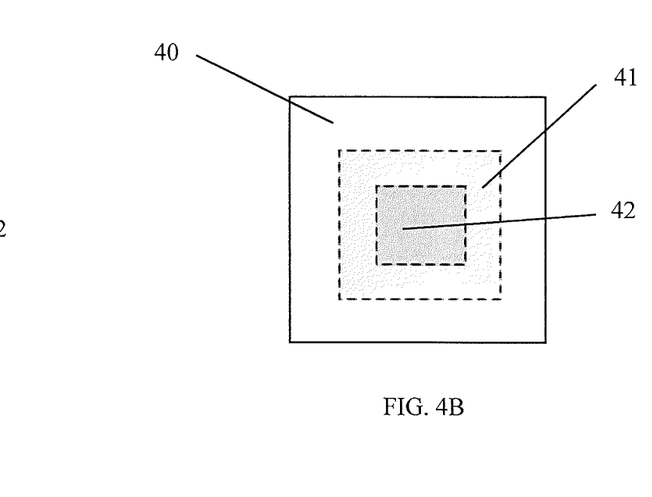
FIG. 4B is a cross-sectional view of the implant depicted in FIG. 4A.

FIGS. 4A and 4B illustrate an embodiment of the density gradient biopolymeric matrix implant containing three homogeneous matrices having densities distinct from each other. For example, matrix 40 can have a density in the range of 0.02 g/cm$^3$ to 0.2 g/cm$^3$, matrix 41 can have a density in the range of 0.2 g/cm$^3$ to 0.6 g/cm$^3$, and matrix 42 can have a density in the range of 0.6 g/cm$^3$ to 1.0 g/cm$^3$.

The three-dimensional density gradient biopolymeric matrix implant described above can be in the shape of, e.g., a cube, a cylinder. The shape is selected depending upon the intended use. One example is a rectangular shape for use as a dura substitute membrane.

Bioactive molecules, e.g., drugs and bioactive macromolecules, can be incorporated into the three-dimensional density gradient biopolymeric matrix implants described above. For example, bone morphogenetic proteins, insulin-like growth factor I, insulin-like growth factor II, laminin, and heparin can be incorporated into the three-dimensional density gradient biopolymeric matrix implants.

The rate of diffusion of any bioactive molecule from the implant is a function of its molecular weight, the densities of the matrices making up the implant, and the physical arrangement of the matrices within the implant, i.e., the diffusion path. A desired diffusion rate can be achieved by forming each matrix at a known density. By controlling the diffusion path and diffusion rate of a bioactive molecule, any desired spatial and temporal dose of the bioactive molecule reaching a target tissue or organ at an implant site can be achieved.

Figure 2A:
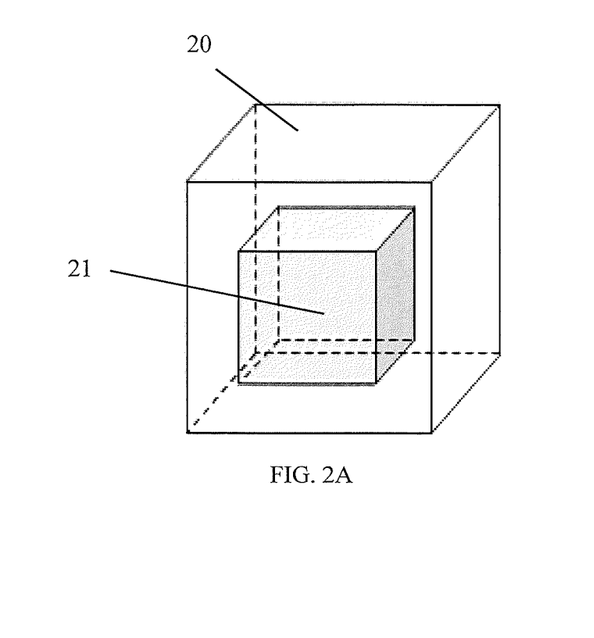
FIG. 2A is a three-dimensional view of another embodiment of a density gradient biopolymeric matrix implant having two different density regions arranged in a cubic geometry.
Figure 2B:
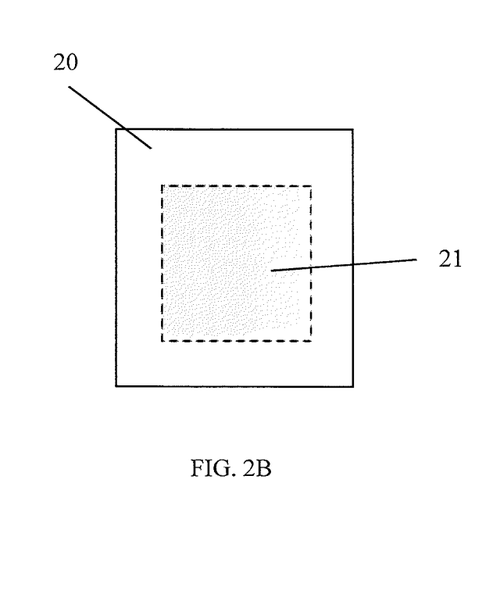
FIG. 2B is a cross-sectional view of the implant depicted in FIG. 2A.
Figure 3A:
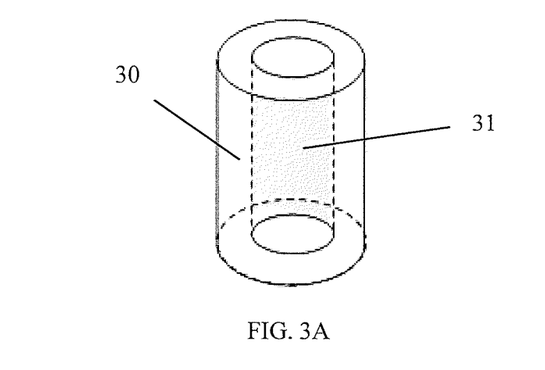
FIG. 3A is a three-dimensional view of yet another embodiment of a density gradient biopolymeric matrix implant having two different density regions arranged in a cylindrical geometry.
Figure 3B:
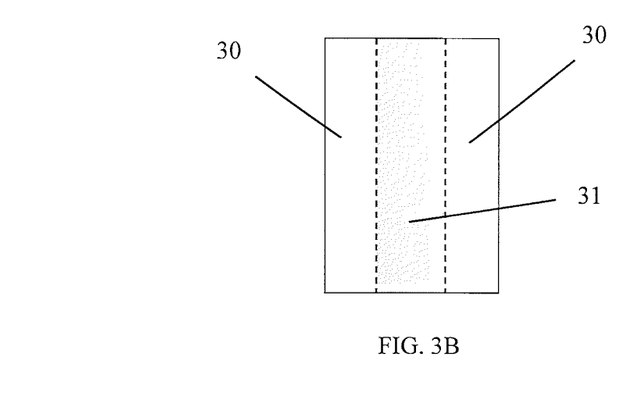
FIG. 3B is a cross-sectional view of the implant depicted in FIG. 3A.

The three-dimensional density gradient biopolymeric matrix implant shown in FIGS. 2A and 2B can be used as a drug carrier for local drug therapy. For example, bioactive molecules can be incorporated into homogeneous matrix 21. After implantation, the bioactive molecules will diffuse out of homogeneous matrix 21 into homogeneous matrix 20. The bioactive molecules become available as they diffuse out of homogeneous matrix 20 and during resorption of homogeneous matrix 20.

The implants described above can be produced by the methods disclosed below.

A first method for preparing a density gradient biopolymeric matrix implant requires an initial step of obtaining a first homogeneous biopolymeric matrix layer. The first homogeneous biopolymeric matrix layer can be formed of biopolymeric fibers. The biopolymeric fibers can be protein or polysaccharide. For example, the biopolymeric fibers can be formed of alginic acid, chitosan, glycosaminoglycan, cellulose, collagen, elastin, and fibrin. In a preferred method, the first homogeneous biopolymeric matrix layer obtained includes biopolymeric fibers formed of fibrillar collagen (e.g., type I, type II, and type III collagen). The collagens can be genetically engineered collagens, collagen from human tissues, collagen from bovine or porcine tissues, and collagen from fish. Type I collagen is particularly preferred.

The first homogeneous biopolymeric matrix layer can be obtained, for example, by adjusting the pH of a biopolymeric fiber suspension to the isoelectric point of the biopolymeric fibers, thereby coacervating the biopolymeric fibers into long fibers, e.g., greater than 50 mm in length. The long fibers can then be compressed and freeze-dried to obtain the first homogeneous biopolymeric matrix layer.

In a second step, a second homogeneous biopolymeric matrix layer is obtained that has a density lower than that of the first homogeneous biopolymeric matrix layer. The second homogeneous biopolymeric matrix layer, like the first homogeneous biopolymeric matrix layer, is formed of the biopolymeric fibers described in the preceding paragraph.

The first and second homogeneous matrix layers thus obtained can both include the same biopolymeric fibers or can each include different biopolymeric fibers. For example, one homogeneous matrix layer can be formed of biopolymeric fibers prepared from a protein and another homogeneous matrix layer can be formed of biopolymeric fibers prepared from a polysaccharide. In a preferred embodiment of the method, all of the biopolymeric fibers are type I collagen fibers.

Next is a step of hydrating the first homogeneous biopolymeric matrix layer. Hydration can be accomplished by various means known in the art. For example, the first homogeneous biopolymeric matrix layer can be soaked in distilled $H_2O$ for 1 to 10 min (e.g., 1, 2, 3, 4, 5, 6, 7, 8, 9, and 10 min.). In a preferred embodiment, the first homogeneous biopolymeric matrix layer is soaked for 5 min.

Not to be bound by theory, it is believed that in order to relax the biopolymeric fibers on the surface of the homogeneous biopolymeric matrix layer, particularly if it contains densely packed biopolymeric fibers, pre-hydration of the homogeneous biopolymeric matrix layer is required. The surface fibers, in the presence of $H_2O$, will relax and be released into a freer state as compared to the dry state where the fibers adhere more strongly to the surface. The hydration step is important to create physical and mechanical interactions between the first and second homogeneous biopolymeric matrix layers, particularly if one of them has a dense matrix.

The physical and mechanical interactions occur as the surface fibers are brought in close contact, resulting in entanglement and physical trapping between fibers from the first matrix and the second matrix. These physical and mechanical interactions are not stable interactions. In other words, they can be separated by physical forces without significantly affecting the respective matrices. In order to stabilize the physical and mechanical interactions, covalent chemical bonds, i.e., cross-links, between the fibers at the interface must be formed. Cross-linking agents effective for bonding the fibers together are described above at page 8, lines 3-13.

As also mentioned above, cross-linking between fibers can be accomplished by dehydrothermal cross-linking without a cross-linking agent if the fibers are formed of protein. Dehydrothermal cross-linking can be performed by incubating the homogeneous biopolymeric matrix layers at 100° C. under a vacuum below 50 mTorr.

Furthermore, an optional step of physically roughening the surface of the first homogeneous biopolymeric matrix layer can be performed in order to increase the number of biopolymeric fibers available for integrating with biopolymeric fibers in the second homogeneous biopolymeric matrix layer. Physical roughening can be achieved, for example, by scraping the surface of the first homogeneous biopolymeric matrix layer with a wire brush.

Alternatively, the hydration step discussed above can be carried out by coating the surface of the first homogeneous biopolymeric matrix layer with an aqueous dispersion of biopolymeric fibers.

After hydrating the first homogeneous biopolymeric matrix layer, it is placed in contact with the second homogeneous biopolymeric matrix layer to form a two-layer matrix. The layers can be placed in contact by placing the first higher density homogeneous biopolymeric matrix layer on top of the second homogeneous biopolymeric matrix layer and applying light pressure such that there are no gaps between the two homogeneous biopolymeric matrix layers.

The two layers, after being contacted with one another, are then freeze-dried. In one particular example, the two-layer matrix is freeze-dried by incubating it for 48 h at −40° C. followed by 18 h at 20° C. at a pressure less than 200 mTorr.

The dried frozen two-layer matrix is then subjected to cross-linking. Exemplary cross-linking agents are set forth at page 8, lines 3-13, supra. In a preferred embodiment, the cross-linking step is accomplished by exposing the freeze-dried two-layer matrix to formaldehyde vapor generated from a 2% HCHO solution.

In an alternative method for producing a density gradient biopolymeric matrix implant having two densities, a first homogeneous biopolymeric matrix layer is obtained followed by a step of preparing a dispersion of biopolymeric fibers. The biopolymeric fibers can be those described at page 5, lines 1-22, supra. Type I collagen fibers are preferred.

The first homogeneous biopolymeric matrix layer is then placed in contact with the dispersion to form a composite matrix having two densities. As mentioned in the method above, light pressure can be applied to the first homogeneous biopolymeric matrix layer such that there are no gaps between it and the dispersion of biopolymeric fibers. In an embodiment, the dispersion is poured into a tray to a thickness of 0.1 mm to 2 mm, preferably 0.05 mm to 0.2 mm. The thickness of the dispersion can be adjusted depending upon the desired thickness of this layer in the composite matrix. The density of this layer can be adjusted by varying the solid content of biopolymeric fibers in the dispersion.

The composite matrix is subjected to freeze-drying as described above.

Finally, the composite matrix, after freeze-drying, is subjected to a cross-linking agent, also as described above. The resulting density gradient biopolymeric matrix implant has two densities, one for the first homogeneous biopolymeric matrix layer and the other density for a second homogeneous biopolymeric matrix layer that was formed from the dispersion of biopolymeric fibers.

In another preferred embodiment, the method includes the steps of (i) obtaining a first homogeneous biopolymeric matrix layer having a first density, (ii) crosslinking the first homogenous biopolymeric matrix layer, (iii) preparing a dispersion of biopolymeric fibers, (iv) placing the first homogeneous crosslinked biopolymeric matrix layer in contact with the dispersion to form a composite matrix, and (v) air drying the composite matrix.

This method can be used advantageously to prepare a density gradient biopolymeric matrix implant having a thin dense layer and a thicker porous layer. For example, the method can be used to form a thin dense layer (e.g., less than 50 µm thick) from the dispersion of biopolymeric fibers while preserving the physical properties of the porous first homogeneous biopolymeric matrix layer.

In another embodiment of the method, a density gradient biopolymeric matrix implant having two thick porous layers (e.g., each layer being 10-20 mm thick) can be prepared by contacting a thick porous homogeneous biopolymeric matrix layer of biopolymeric fibers with a thick dispersion of biopolymeric fibers, followed by the freeze-drying and cross-linking steps described above. Notably, the contact time of the thick porous homogeneous biopolymeric matrix layer with the dispersion need be carefully controlled so that the junction of the two matrices is not too wide. For example, a contact time of 5 to 20 s (e.g., 5, 10, 15, and 20 s) prior to the freeze-drying step will be sufficient to achieve a good integration of the two matrices.

A density gradient biopolymeric matrix implant having three distinct layers can be prepared by performing additional steps prior to the cross-linking step described, supra. More specifically, a second biopolymeric fiber dispersion is prepared and contacted with the freeze-dried composite matrix. The contacting step is carried out by placing the freeze-dried composite matrix on the second biopolymeric fiber dispersion, applying light pressure to the freeze-dried composite matrix such that there are no gaps between it and the second dispersion of biopolymeric fibers. A freeze-drying step is then carried out, followed by a cross-linking step. These last two steps, carried out as described above, lead to the formation of a density gradient biopolymeric matrix implant having three matrix layers.

As mentioned above, bioactive molecules can be incorporated into the density gradient matrix implant. This can be achieved, for example, by incorporating small molecules, e.g., antibiotics, into the dispersion of biopolymeric fibers used to form the second homogeneous matrix layer of the implant. After freeze-drying, the bioactive molecules will be retained within the matrix layer formed from the dispersion.

On the other hand, larger bioactive macromolecules can be directly incorporated into the homogeneous biopolymeric matrix layer such that physical entrapment and mechanical entanglement with the biopolymeric fibers in the layer occurs during the coacervation of the biopolymers at the isoelectric point.

Without further elaboration, it is believed that one skilled in the art can, based on the description above, utilize the present invention to its fullest extent. The specific examples below are to be construed as merely illustrative, and not limitative of the remainder of the disclosure in any way whatsoever.

EXAMPLES

Example 1: Preparation of Purified Type I Collagen Fiber Dispersion

Bovine deep flexor tendon was cleaned by removing fat and fascia and by washing with $H_2O$. The cleaned tendon was frozen and comminuted into 0.5 mm slices with a meat slicer. One kilogram of the sliced wet tendon was subsequently extracted with 5 L of distilled $H_2O$ ($dH_2O$) at room temperature for 24 h, followed by 5 L of 0.2 N HCl/0.5 M $Na_2SO_4$ also at room temperature for 24 h. The extraction solution was discarded.

The residual acid in the extracted tendon was removed by washing with 5 L of a 0.5M $Na_2SO_4$ solution. The tendon was then extracted with 5 L of a 1.0 M NaOH/1 M $Na_2SO_4$ solution at room temperature for 24 h. The extraction solution again was discarded. Any residual base was neutralized by adding a 0.05 N HCl solution to achieve a pH of 5, followed by several washes with $dH_2O$ to remove residual salts in the purified tendon. The tendon was then defatted for 8 h with 5 volumes of isopropanol at room temperature under constant agitation, followed by an overnight treatment at 25° C. with an equal volume of isopropanol. The resulting insoluble collagen fiber preparation was equilibrated in 0.05 M phosphate buffer, pH 7.4 for 24 h. Excess phosphate buffer was decanted and the purified collagen fibers were freeze dried and stored.

Example 2: Preparation of Acid Dispersed Collagen Fibers

An aliquot of the insoluble collagen fibers prepared as described in Example 1 was weighed and dispersed in 0.07 M lactic acid, homogenized with a Silverson homogenizer (East Longmeadow, Mass.), and filtered with a 40 mesh stainless steel mesh filter to obtain a dispersion containing 0.7% (w/v) collagen. The dispersion was de-aerated under vacuum to remove any air trapped in the dispersion.

Example 3: Preparation of a High Density Matrix

One liter of acid dispersed collagen fibers prepared as described in Example 2 was placed in a beaker and reconstituted by adjusting the pH to the isoelectric point of collagen, i.e., pH 5.0, by adding 100 ml of 0.3% $NH_4OH$. The reconstituted collagen fibers were removed from the beaker and placed on a 20 mesh stainless steel screen. Excess solution was removed by slowly moving the reconstituted fibers back and forth over the mesh with a teflon spatula until the solid content of the reconstituted collagen fibers was between 5% to 20% by weight. The partially dehydrated collagen fibers, having dough-like properties, were then placed under a roller to compress the collagen dough to a thickness of 0.5 mm, thereby forming a compressed collagen matrix.

An aliquot of the compressed collagen fiber matrix was freeze-dried by first incubating it for 24 h at −10° C. followed by 6 h at 20° C. at a pressure less than 200 mTorr using a Virtis freeze dryer (Gardiner, N.Y.). The freeze-dried collagen matrix was cross-linked at 22° C. for 3 to 6 h with formaldehyde vapor generated from a 2% HCHO solution. The cross-linked matrix was extensively rinsed in $dH_2O$ and freeze-dried again to obtain a collagen matrix having a density of 0.3 $g/cm^3$ to 1.0 $g/cm^3$.

Example 4: Preparation of a Low Density Porous Matrix

Ten grams of purified type I collagen fibers prepared as described in Example 1 was dispersed in 1 L of 0.0015 M NaOH for 20 h. The collagen fiber dispersal was homogenized with a Silverson homogenizer, filtered through a 100 mesh stainless steel filter, and de-gassed under vacuum. The dispersion was then neutralized by adjusting the pH to 7-9 by adding 0.05 M HCl. The neutralized collagen dispersion was then centrifuged at 3000 rpm at 4° C. for 2 min. The collagen fiber dispersion was transferred to a beaker after decanting 250 ml of supernatant. The dispersion was mixed, de-gassed under vacuum, and poured into a tray to prepare a 4 mm thick matrix. The collagen matrix in the tray was freeze-dried as described in Example 3. The freeze-dried collagen matrix was cross-linked at 22° C. for 60 min. with formaldehyde vapor generated from a 2% HCHO solution. The cross-linked matrix was placed under a vacuum to remove any residual cross-linking agent. The cross-linked low density porous collagen matrix thus prepared had a density of 0.02 g/cm$^3$ to 0.03 g/cm$^3$ and average pore size of 250 µm to 600 µm.

Example 5: Forming a Dual-density Matrix Implant

The high density collagen matrix described in Example 3 was hydrated by soaking it in dH$_2$O for 5 min. The low density porous collagen matrix described in Example 4 was laid on the surface of the hydrated high density collagen matrix. Light pressure was applied to the top of the porous collagen matrix such that no gaps were seen between the two matrices. The opposed matrices were immediately freeze-dried. The freeze-dried matrices were cross-linked at 22° C. for 3 h with formaldehyde vapor generated from a 2% HCHO solution. The dual-density matrix thus formed was vented for 24 h to remove any remaining formaldehyde and characterized as described below.

Example 6: Alternative Method for Forming a Dual-density Matrix Implant

A low density porous matrix was produced from alkaline dispersed collagen fibers as described above in Example 4.

An acidic dispersion of collagen fibers produced as described above in Example 2 was poured onto a freeze-drying tray to a thickness of 5 mm. The low density porous matrix was placed on top of the acidic dispersion of collagen fibers and gently compressed to achieve full contact between the low density porous matrix and the dispersion. The resulting implant precursor was immediately freeze-dried. The freeze-dried material was subjected to cross-linking at 22° C. for 3 h with formaldehyde vapor generated from a 2% HCHO solution. The dual-density matrix thus formed was vented for 24 h to remove any remaining formaldehyde and characterized as described below. The density of the high density layer was in the range of 0.3 g/cm$^3$ to 1.0 g/cm$^3$.

Example 7: Another Alternative Method for Forming a Dual-density Matrix Implant

A low density porous matrix was produced from alkaline dispersed collagen fibers as described above in Example 4. The low density porous matrix was subjected to cross-linking at 22° C. for 1 h with formaldehyde vapor generated from a 0.5% HCHO solution. The crosslinked low density porous sponge was vented for 24 hr to remove any remaining formaldehyde. An acidic dispersion of collagen fibers produced as described above in Example 2 was poured onto a freeze-drying tray to a thickness of 1 mm. The low density porous matrix was placed on top of the acidic dispersion of collagen fibers and gently compressed to achieve full contact between the low density porous matrix and the dispersion. The resulting implant precursor was air-dried.

Example 8: Characterization of a Density Gradient Matrix Implant

A. Density Testing

Samples of the density gradient matrix implant were dried under P$_2$O$_5$ for 24 h and the dry weight recorded. The density of the high density layer and low density layer were determined separately. The dimensions of the sample were measured with a caliper to calculate its volume. The density was determined as the weight of the product per unit volume.

B. Liquid Permeability Testing

Samples were placed between two chambers of a specially designed apparatus and clamped to provide a tight seal. A fixed volume of dH$_2$O was added to the opening of one chamber and the amount of dH$_2$O that passed through the membrane in 1 min was recorded. If all of the dH$_2$O passed through immediately, a time of less than 1 min. was recorded. The liquid permeability was calculated as the volume of dH$_2$O that passed through the sample and divided by time and the area of the opening in the apparatus.

C. Scanning Electric Microscopy

Both the low density side and the high density side of the density gradient matrix implant were prepared for electron microscopy by carbon-coating. Micrographs were obtained using a scanning electron microscope (JEOL Ltd. Model JSM 6100).

D. Peel Strength Testing:

The density gradient matrix implant was cut into 1 in. wide sections. The length of the samples was 2 in. The low density side and the high density side were each clamped to the grips of a mechanical tester (Chatillon model TCD-200/DFS-010). The peak tension at which the two sides pulled apart was recorded. The peel strength was calculated as the peak tension divided by the width of the sample.

Analysis of the density gradient matrix implant prepared as described in Examples 6 and 7 revealed the characteristics shown in the following table.

TABLE 1

Physical properties of the density gradient matrix implant

| Characteristics | low density side | high density side |
| --- | --- | --- |
| Density (g/cm$^3$) | 0.015 ± 0.003 | 0.32 ± 0.03 |
| Liquid permeability (ml/min/cm$^2$) | 2.64 ± 0.03 | 0.010 ± 0.002 |
| Pore size (µm) | 50 to 500 | <1 |

The peel strength of the density gradient matrix implant was 0.42±0.09 kgf/in.

Example 9: Repair of Dura Mater Using a Density Gradient Matrix Implant Having Two Densities The density gradient matrix implant having two densities was tested for efficacy in a rabbit duraplasty model. The implant, as described above, is formed of a high density collagen matrix with low permeability integrated with a low density porous matrix. It was surgically implanted according to established protocols. See, e.g., Lee, et. al., Two Novel Collagen Based Dura Repair Membranes: Solutions for the Multifaceted Needs in Duraplasty Part II: In Vivo Rabbit Duraplasty Studies, 10th World Biomaterial Congress, Montreal, Canada, May 2016 ("Lee et al.").

Experimental animals were euthanized at 4, 8, 13, 16, and 20 weeks and analyzed for evidence of cerebral fluid (CSF) leakage. Gross observations of the implant site were also made. Tissue at the implant site was harvested and analyzed by histology according to established grading systems. See Lee et al.

Histology sections were analyzed by a veterinary pathologist for the following parameters, based on US Food and Drug Administration guidance document for dural substitutes: (i) local tissue reaction immediately surrounding the implant; (ii) implant resorption and replacement by host tissue; (iii) implant vascularization; (iv) microscopic evidence of infection; (v) evidence of hydrocephalus; (vi) hemorrhage, (vii) foreign body reaction; and (viii) any other abnormal tissue reactions.

The density gradient matrix implant was effective as a dura substitute in the rabbit duraplasty model. There was no evidence of infection or hydrocephalus in any of the implant sites. The density gradient matrix implant was resorbed over time and aided in new collagen deposition. The new collagen deposited around the implant site consisted of one or more layers of mature fibrous connective tissue. The new collagen deposition started at the edge of the native dura and spread to the middle of the implant sites. The density gradient matrix implant was biocompatible, showing no significant abnormal tissue reaction. In sum, the density gradient matrix implant is an effective dura substitute matrix in duraplasty procedures. The dense matrix portion of the density gradient matrix implant provides the added benefit of minimizing the potential risk of CSF leakage post-surgery.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. A method for preparing a density gradient biopolymeric matrix implant, the method comprising:
   obtaining a first homogeneous biopolymeric matrix layer having a first density and having a first surface and a second surface opposed to the first surface, the first homogeneous biopolymeric matrix layer being formed of first biopolymeric fibers;
   obtaining a second homogeneous biopolymeric matrix layer having a second density lower than the first density and having a first surface and a second surface opposed to the first surface, the second homogeneous biopolymeric matrix layer being formed of second biopolymeric fibers;
   hydrating the first homogeneous biopolymeric matrix layer,
   placing in contact the first surface of the hydrated first homogeneous biopolymeric matrix layer with the first surface of the second homogeneous biopolymeric matrix layer such that the first biopolymeric fibers at the first surface of the first homogeneous biopolymeric matrix layer are entangled and physically trapped with the second biopolymeric fibers at the first surface of the second homogeneous biopolymeric matrix layer, thereby forming a two-layer matrix,
   freezing the two-layer matrix,
   drying the frozen two-layer matrix, and
   cross-linking the dried frozen two-layer matrix,
   wherein the hydrating step is carried out by coating the first surface of the first homogeneous biopolymeric matrix layer with an aqueous dispersion of biopolymeric fibers, whereby the dispersed biopolymeric fibers are cross-linked to both the first surface of the hydrated first homogeneous biopolymeric matrix layer and the first surface of the second homogeneous biopolymeric matrix layer.

2. The method of claim 1, wherein the first biopolymeric fibers and the second biopolymeric fibers are collagen fibers.

3. The method of claim 2, wherein the collagen fibers are type I collagen fibers.

4. A method for preparing a density gradient biopolymeric matrix implant, the method comprising:
   obtaining a first homogeneous biopolymeric matrix layer having a first density, the first homogeneous biopolymeric matrix layer being formed of first biopolymeric fibers,
   preparing a dispersion of biopolymeric fibers,
   placing the first homogeneous biopolymeric matrix layer in contact with the dispersion to form a composite matrix in which the first biopolymeric fibers are entangled and physically trapped with biopolymeric fibers in the dispersion,
   freezing the composite matrix,
   drying the frozen composite matrix,
   preparing a second biopolymeric fiber dispersion,
   contacting the dried frozen composite matrix with the second biopolymeric fiber dispersion to form a three-part composite matrix,
   freezing the three-part composite matrix,
   drying the frozen three-part composite matrix, and
   cross-linking the dried frozen composite matrix, whereby the cross-linking step forms a three-part density gradient biopolymeric matrix implant.

5. The method of claim 4, wherein the first homogeneous biopolymeric matrix layer is formed of cross-linked collagen fibers, the biopolymeric fibers are collagen fibers, and the second biopolymeric fiber dispersion is a collagen fiber dispersion.

6. The method of claim 5, wherein the first homogeneous biopolymeric matrix layer is formed of cross-linked type I collagen fibers, the biopolymeric fibers are type I collagen fibers, and the second biopolymeric fiber dispersion is a type I collagen fiber dispersion.

* * * * *